United States Patent [19]

Harris

[11] Patent Number: 5,210,257
[45] Date of Patent: May 11, 1993

[54] PREPARATION OF ARYL COMPOUNDS CONTAINING CARBOXYL AND SULFONYL GROUPS

[75] Inventor: William J. Harris, Midland, Mich.

[73] Assignee: The Dow Chemical Company, Midland, Mich.

[21] Appl. No.: 685,257

[22] Filed: Apr. 12, 1991

[51] Int. Cl.$^5$ .................. C07C 65/105; C07C 323/20; C07C 323/21; C07C 309/32

[52] U.S. Cl. ...................................... 558/49; 558/51; 558/52; 560/10; 560/11; 560/12; 560/14; 560/17; 560/18; 562/26; 562/27; 562/29; 562/41; 562/42; 562/46; 562/56; 562/57; 562/426; 562/427; 562/429; 562/430; 562/432; 564/85; 564/86; 564/88; 564/162

[58] Field of Search ...................... 562/41, 42, 45, 46, 562/47, 828, 832, 833, 834, 56, 432, 473, 474, 26, 29, 57, 840, 426, 427, 429, 430, 27; 560/9, 10, 11, 18, 17, 64, 65, 66, 12, 14; 564/85, 86, 88, 162; 558/49, 51, 52

[56] References Cited

U.S. PATENT DOCUMENTS

| | | |
|---|---|---|
| 3,077,492 | 2/1963 | Horn . |
| 3,164,567 | 1/1965 | Horn . |
| 3,166,531 | 1/1965 | Horn . |
| 3,953,400 | 4/1976 | Dahl . |
| 4,229,564 | 10/1980 | Dahl . |
| 4,278,616 | 7/1981 | Wineholt et al. ............. 562/41 |
| 4,596,680 | 6/1986 | Jost et al. . |
| 4,655,975 | 4/1987 | Snoble . |
| 4,704,448 | 1/1987 | Brugel . |

FOREIGN PATENT DOCUMENTS

| | | |
|---|---|---|
| 8502013 | 10/1985 | European Pat. Off. . |
| 9003995 | 4/1990 | European Pat. Off. . |

OTHER PUBLICATIONS

Moskvichev et al. Zh. Org. Khum., 1982, 18(5), 1006-10.
CA(97)91863a.
"Synthesis of Aromatic Polyetherketones in Trifluoromethanesulphonic Acid", H. M. Colquhoun and D. F. Lewis, pp. 1902-1908 of *Polymer*, vol. 29, Oct. 1988.
"Synthesis of Polyetherketones in Trifluoromethanesulphonic Acid:Some Structure-Reactivity Relationships", H. M. Colquhoun, pp. 17-18 of *ACS Polymer Preprints*, vol. 25(2), 1984.
"Synthesis of Poly(Phenylene Ether Sulfone) by Direct Self-Polycondensation of Sodium 4-Phenoxybenzenesulfonate Using Phosphorous Pentoxide/Methanesulfonic Acid as Condensing Agent and Solvent", Ueda, pp. 271-274, Makromol Chem, Rapid Commun (6), 1985.
"Synthesis of Polyketones by Direct Polycondensation of Dicarboxylic Acids with Diaryl Compounds Using Phosphorus Pentoxide/Methanesulfonic Acid As Condensing Agent and Solvent", by M. Ueda and T. Kano, pp. 833-836 of *Makromol Chem*, Rapid Commun, vol. 5 (1985).
"Synthesis of Poly(benzoxazole(s by Direct Polycondensation of Dicarboxylic Acids with 3,3'-Dihydroxybenzidine Dihydrochloride Using Phosphorus Pentoxide/Methanesulfonce Acid as Condensing Agent and Solvent", by M. Ueda, H. Sugita and M. Sato, pp. 1019-1026 in *Journal of Polymer Science: Part A: Polymer Chemistry*, vol. 24(1986).
"Synthesis of Poly(benzothiazole)s by Direct Polycondensation of Dicarboxylic Acids with 2,5-Diamino-1,-4-benzenedithiol Dihydrochloride Using Phosphorus Pentoxide/Methanesulfonic Acid as Condensing Agent and Solvent", by M. Ueda, S. Yokote and M. Sato., pp. 117-122 in *Polymer Journal*, vol. 18, No. 2 (1986).
"Poly(benzimidazole) Synthesis by Direct Reaction of Diacids and Tetramine" by M. Ueda, M. Sato and A. Mochizuki, pp. 2723-2726 in Macromolecules, vol. 18 (1985).
"Synthesis of Aromatic Poly(ether ketones) in Phosphorus Pentoxide/Methanesulfonic Acid" by M. Ueda and M. Oda on pp. 673-679 Polymer Journal vol. 21, 1989.
"Synthesis of Aromatic Poly(etherketones)", Ueda, Sato, pp. 2675-2678 *Macromolecules* vol. 20 ('87).
U.S. Defensive Pub. #835,295, Lappin et al., Nov. 18, 1969.

*Primary Examiner*—Marianne M. Cintins
*Assistant Examiner*—Margaret Page

[57] ABSTRACT

Novel aryl ethers, containing both a carboxylic acid and a sulfonic acid functionality; and a process for making them are described. These difunctional aryl compounds comprise:
i) a carboxylic acid group or its derivative,
ii) a first aromatic group bonded to the carboxylic acid or its derivative,
iii) a second aromatic group linked to the first aromatic group by a non-electron-withdrawing moiety,
iv) a third aromatic group linked to the second aromatic group by a non-electron-withdrawing moiety, and
v) a sulfonyl group or its derivative bonded to the third aromatic group.

17 Claims, No Drawings

PREPARATION OF ARYL COMPOUNDS CONTAINING CARBOXYL AND SULFONYL GROUPS

STATEMENT OF GOVERNMENT RIGHTS

This invention was made with Government support under contract number F33615-86-C-5068 awarded by the United States Air Force. The Government has certain rights in this invention.

BACKGROUND OF INVENTION

This invention relates to the art of reactive difunctional acid compounds.

Polybenzazole ("PBZ") polymers, such as polybenzoxazole ("PBO"), polybenzimidazole ("PBI") or polybenzothiazole ("PBT"), are a known class of polymers which are typically formed and fabricated in strongly dehydrating protic acid solvents. See e.g. Wolfe et al., *Liquid Crystalline Polymer Compositions, Processes and Products*, U.S. Pat. No. 4,533,693 (Aug. 6, 1985) and 11 Ency. Poly. Sci. & Eng., *Polybenzothiazoles and Polybenzoxazoles*, 601 (J. Wiley & Sons 1988).

In order to modify the properties of the PBZ polymers so that they will function adequately for various end use applications it is desirable to make copolymers of PBZ's and thermoplastic polymers. One such thermoplastic polymer is a polyarylethersulfone. See e.g. International Publication No. WO90/03995 entitled *Copolymers Containing Polybenzoxazole, Polybenzothiazole and Polybenzimidazole Moieties.*

A strongly protic acid solvent/initiator medium is usually required for any type of polymerization with PBZ monomers, because PBZ polymers and copolymers require such an environment in order to react and remain in solution once formed. Therefore, in order to make copolymers of PBZ it is required that all reagents must be able to function in a strong protic acid solvent system.

Heretofore, such copolymers of PBZ's have been difficult, if not impossible to prepare, because of the lack of known reagents that were capable of reacting and remaining in solution in the strongly protic acid solvents required.

SUMMARY OF THE INVENTION

One aspect of the present invention is a difunctional aryl compound comprising:
1. a carboxylic acid group or its derivative,
2. a first aromatic group bonded to the carboxylic acid or its derivative,
3. a second aromatic group linked to the first aromatic group by a non-electron-withdrawing moiety,
4. a third aromatic group linked to the second aromatic group by a non-electron-withdrawing moiety,
5. a sulfonyl group or its derivative bonded to the third aromatic group.

A second aspect of the present invention is a process to prepare the above described difunctional aryl compound by reaction of methyl 4-(4-phenoxyphenoxy)benzoate with a sulfonating agent under conditions such that the above described difunctional aryl compound is formed.

A third aspect of the present invention is a process for synthesizing a polymer comprising the step of contacting the compound of the present invention or a dimer of that compound with at least one comonomer having a plurality of decoupled nucleophilic aromatic rings in a dehydrating protic acidic medium under conditions suitable to initiate Friedel-Crafts polymerization.

The difunctional aryl compound which forms the first aspect of the present invention is synthesized by the process of the second aspect of the present invention. The difunctional aryl compounds are useful in forming copolymers such as those prepared by the third aspect of the present invention. The copolymers formed via the process of the third aspect of the present invention can be formed into useful shaped articles such as fibers and films. These fibers and films can then be used in items such as composites and laminates to impart desirable properties to those composites and laminates.

DETAILED DESCRIPTION OF THE INVENTION

The difunctional aryl compounds of this invention contain aromatic groups. These aromatic groups include any aromatic group capable of being attached to either a carboxylic acid group or its derivative, a sulfonyl group or its derivative or a non-electron-withdrawing moiety. Each aromatic group may be polycyclic but each is preferably monocyclic. Each aromatic group is preferably carbocyclic and more preferably hydrocarbocyclic. Each aromatic group preferably contains no more than one substituent, in order to minimize steric hindrance about reactive sites. It is more preferably unsubstituted. However, when desired, aromatic groups with multiple substituents can be selected for inclusion in the compound in order to have substituents already present on locations on the individual aromatic group where aromatic electrophilic substitution is unwanted. Examples of preferred aromatic groups include divalent groups such as arylene, e.g., phenylene, naphthenylene and biphenylene. A phenylene group is the most preferred aromatic group in the present invention.

Non-electron-withdrawing moieties connect the aromatic groups in the present invention. By "non-electron-withdrawing" it is meant an electron donating or a neutral group. The carboxylic acid group and the sulfonic acid group in the diacid compound deactivate each other with respect to Friedel-Crafts reactions in protic acid solutions. The non-electron-withdrawing moieties decouple the two acid groups and shields them from deactivation or minimizes their deactivation. Deactivation and decoupling are described in further detail in the two articles written or co-written by H. M. Colquhoun entitled, "Synthesis of Aromatic Polyetherketones in Trifluoromethanesulphonic Acid" as printed on pp. 1902–1908 of *Polymer*, Vol. 29, October 1988 and "Synthesis of Polyetherketones in Trifluoromethanesulphonic Acid: Some Structure -Reactivity Relationships", as printed on pp. 17–18, of *ACS Polymer Preprints*, Vol. 25(2), 1984 which are incorporated herein by reference. These articles discuss in detail the considerations that must be given to selecting non-electron-withdrawing moieties with care, to enable desired reactions in compounds that contain aromatic groups linked together by linking groups. Suitable non-electron-withdrawing moieties comprise, for example, a bond or a sulfur atom (thioether) or an oxygen atom (ether linkage). The non-electron-withdrawing moiety may further comprise an aromatic group and a second ether or thio-ether linkage. A preferred non-electron-withdrawing moiety is an oxygen atom (an ether linkage).

The non-electron-withdrawing moieties can be attached to the aromatic groups in any position. It is preferred that they are attached in a para position with respect to each other. The para isomers react better, leading to less side-reactions, than do the others.

A carboxylic acid group or its derivative and a sulfonyl group or its derivative are attached to different aromatic groups in the difunctional aryl compound. The carboxylic acid group or its derivative and the sulfonyl group or its derivative are useful for reacting with other comonomers to form copolymers. The derivative of the carboxylic acid group or the sulfonyl group can be an acid halide, a lower alkyl ($C_1$–$C_6$) ester (preferably a methyl, ethyl, propyl or butyl ester), an amide, an aryl ester, or a corresponding thioester. The preferred derivative is the acid halide, such as an acid chloride, acid bromide or acid iodide, and the preferred acid halide is the acid chloride. The derivative of the carboxylic acid group and the derivative of the sulfonyl group may be, but do not have to be, identical in the same difunctional aryl compound.

The carboxylic acid or its derivative and the sulfonyl group or its derivative are attached to different aromatic groups in any position relative to the non-electron-withdrawing moieties that connect the aromatic groups. It is preferred that they are attached in the para position relative to the non-electron-withdrawing moieties so that the structure of the difunctional aryl compound is primarily linear. The primarily linear structure of the difunctional aryl compound is important so that copolymers made with the difunctional aryl compound are also primarily linear. A linear structure in these copolymers is important so that it is possible to construct copolymers with long chains, leading to high molecular weight copolymers. A high molecular weight is a desired feature of these copolymers.

The diacid compounds of the present invention are preferably represented by the formula:

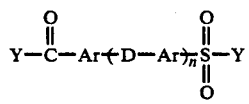

wherein

Each Ar is independently a divalent aromatic group,
each D is independently a non-electron-withdrawing moiety,
n is 2 or more, and
each Y is independently —OH, —Cl, —Br, I, $NH_2$ or OR, where R=a lower alkyl group ($C_1$–$C_6$) or an aryl group.

A general method for manufacturing these difunctional aryl compounds is to add a sulfonating agent to a starting material such as methyl 4-(4-phenoxyphenoxy) benzoate under conditions such that the sulfonyl group is attached to an aromatic group different from the aromatic group to which the methyl ester is attached.

Sulfonyl groups can be added at any unsubstituted position on any aromatic group in the methyl phenoxyphenoxybenzoate ester compound. It is most preferred that the sulfonyl group is attached to the third aromatic group at the para position to the nearest non-electron-withdrawing moiety. Reactions at the 2,3,5 or 6 positions of the aromatic groups can be minimized by controlling the stoichiometry of the reactants in the sulfonating reaction as mentioned in the article by Ueda entitled, "Synthesis of Poly(phenylene ether sulfone) by Direct Self-polycondensation of Sodium 4-phenoxybenzenesulfonate Using Phosphorus Pentoxide/Methanesulfonic Acid as Condensing Agent and Solvent, " *Makromol. Chem., Rapid Commun.* 6, 271–274 (1985).

Once it has been formed, the sulfonated methyl phenoxyphenoxybenzoate ester compound is then hydrolyzed using a mixture of base in alcohol and water followed by the addition of HCl which converts the base salts to the desired carboxylic acid and the sulfonic acid. The resulting (phenoxy-carboxylic-acid-phenoxy-sulfonic-acid-benzene) compound can be converted to the acid chloride derivative of the carboxylic acid group and the sulfonyl group by any of the standard methods known in the art to make an acid chloride. One such method is to react this material with thionyl chloride.

The following formulae illustrate one example of the synthesis.

1. Reaction of Starting Compound With Sulfonating Agent

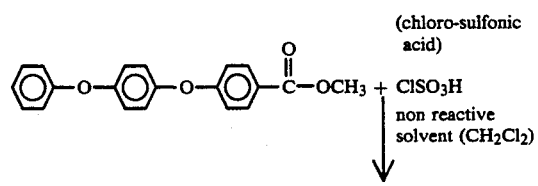

2. Hydrolysis Reaction

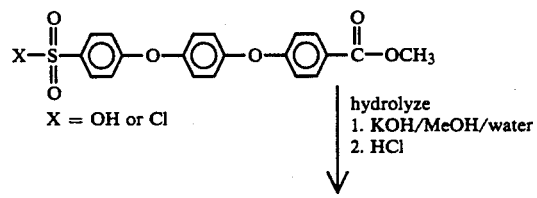

X = OH or Cl hydrolyze
1. KOH/MeOH/water
2. HCl

3. Acid Chloride Reaction

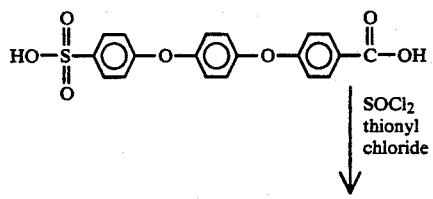

SOCl₂
thionyl chloride

4. Product

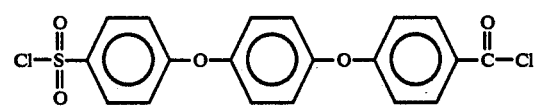

Even though chlorosulfonic acid is effective as the sulfonating agent in the first reaction of the preceding synthesis, it is anticipated that a wide variety of sulfonating agents, e.g., sulfur trioxide, or concentrated sulfuric acid, could be used to sulfonate the starting compound.

Compounds of the present invention are useful for making polymers by a Friedel-Crafts type process. The compounds can be reacted with a comonomer that contains two aromatic groups linked by a suitable non-electron-withdrawing group. Exemplary comonomers include m- or p-diphenoxybenzene and 3- or 4-phenoxybiphenyl. This reaction may be carried out in an organic solvent in the presence of a Lewis Acid catalyst under known conditions. Preferably, however, the reaction is carried out in a dehydrating protic acid, such as polyphosphoric acid or a mixture of methanesulfonic acid and phosphorus pentoxide. The temperature is preferably at least about 25° C. and more preferably at least about 40° C. It is preferably no more than about 100° C. and more preferably no more than about 70° C. Suitable comonomers and reaction conditions are described in the references of Colquhoun which are previously incorporated by reference.

The compounds of the present invention may also be reacted to form a dimer before they are contacted with a comonomer in a polymerization reaction. For instance, two moles of the compound of the present invention may be reacted with one mole of: 4,6-diaminoresorcinol (hereinafter referred to as BB-PBZ monomer): 2,5-diaminohydroquinone: 1,4-dithio-2,5-diaminobenzene: or an equivalent compound to form a dimer having two sulfonic acid groups or derivatives of sulfonic acid. Equivalent reagents are listed in U.S. Pat. No. 4,533,693 at Tables 1-3, which are incorporated herein by reference.

Although all reactions of the difunctional acid compound described herein may take place in a mixture of methanesulfonic acid and phosphorus pentoxide, it is also possible for these reactions to take place in another mixture, e.g., AlCl$_3$ in an appropriate Friedel Crafts solvent (nitrobenzene or ortho-dichlorobenzene) or other strong acids such as polyphosphoric acid or even trifluoromethane sulfonic acid.

The step-by-step dimer reaction (first with BB-PBZ monomer, then with a comonomer) described above is depicted in the following reaction schemes.

1. Reaction of diacid chlorode aryl compound with diaminoresorcinol dihydrochloride to form dimer

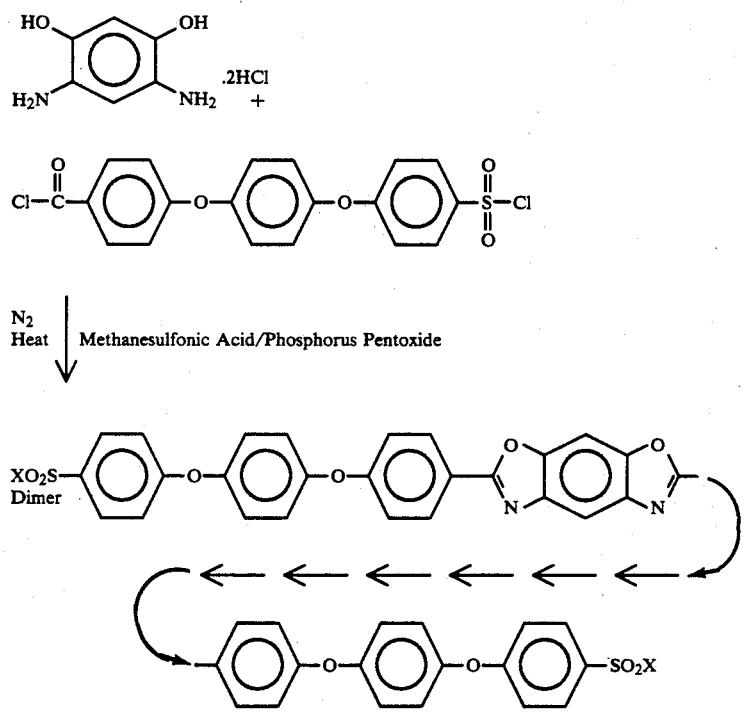

2. Polymerization Reaction

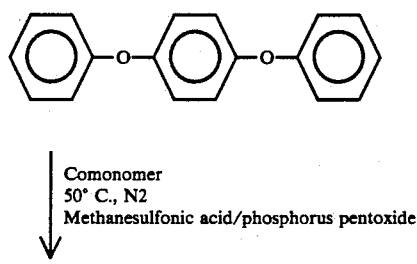

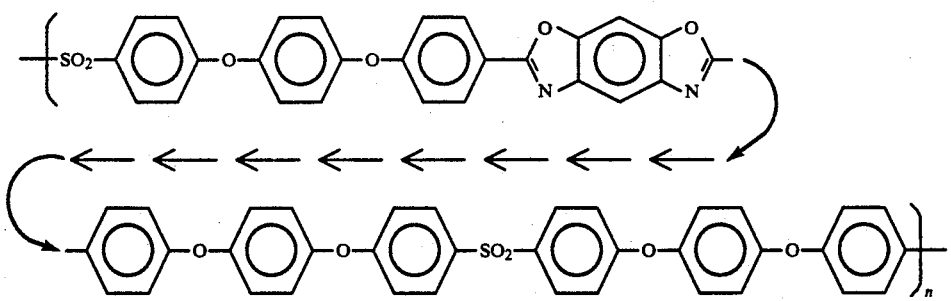

The following examples are given to illustrate the invention and should not be construed as limiting its scope. All parts and percentages are by weight unless otherwise indicated.

EXAMPLE 1 Synthesis of the Diacid Aryl Compound

A mixture of 9.00 g(28.1 mmol) of methyl 4-(4-phenoxyphenoxy) benzoate in 150 mL of methylene chloride is cooled to 0° C. under nitrogen atmosphere with stirring. A solution of 1.87 mL (3.27 g, 28.1 mmol) of chlorosulfonic acid in 50 mL of methylene chloride is added dropwise over a period of 15 minutes. The cooling bath is removed and the mixture is stirred for 14 hours. The precipitate is filtered, washed with 100 mL of methylene chloride and dried in air. It is mixed in a slurry with 120 mL of methanol, 60 mL of water, and 10.0 g of potassium hydroxide, and the slurry is refluxed for two hours. The cooled solution is quenched in aqueous HCl, filtered, washed with 100 mL of cold water, and dried in air. The product is recrystallized from 600 mL of a 5-1 by volume methanol-water solution and dried at 100° C. under vacuum to yield 10.84 g(91%) of 1-(phenoxy-4-carboxylic acid)-4-(phenoxy-4-sulfoniic acid) benzene which has the following structure.

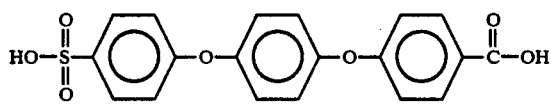

EXAMPLE 2 Conversion of the Diacid Aryl Compound to the Diacidchloride of the Difunctional Aryl Compound A slurry of 10.00 g(25.9 mmol) of 1-(phenoxy-4-carboxylic acid)-4-(phenoxy-4-sulfonic acid) benzene in 250 mL of thionyl chloride and 0.50 mL of N,N-dimethylformamide is refluxed under nitrogen atmosphere for 16 hours with stirring. The slurry is cooled to 20° C. and added to 3L of anhydrous n-hexane. The resulting precipitate is filtered, washed with n-hexane and dried under nitrogen atmosphere. It is stirred with 100 mL of anhydrous methylene chloride and filtered, and 900 mL of anhydrous n-hexane is added to the filtrate. The resulting solution is sealed and cooled to −15° C. The product is filtered and dried under nitrogen atmosphere to yield 7.26 g (66 percent yield) of product. The product obtained can be converted to the dimethyl diester by refluxing with methanol under nitrogen atmosphere in anhydrous methylene chloride, if desired.

EXAMPLE 3 Copolymerization of Difunctional Aryl Compound with Cis-PBO Dope

A mixture of 0.30g(1.41 mmoles) of 4,6-diaminoresorcinol di(hydrogen chloride) and 1.84g(4.35 mmoles) of 1-(4-chlorocarbonylphenoxy)-4-(4-chlorosulfonylphenoxy) benzene is stirred under nitrogen atmosphere. A 134.82-g solution containing a 10-1 mixture by weight of methanesulfonic acid and phosphorus pentoxide is added, and the mixture is warmed to 70° C. for 2 hours. The temperature is raised to 90° C. for 16 hours. A 25.00-g portion of dope was added containing polyphosphoric acid and about 14 weight percent cis-PBO polymer. The cis-PBO polymer dope is made according to the instructions contained in Example 1, pp. 135–137 of pending U.S. patent application Ser. No. 407,973, filed Sep. 15, 1989, Attorney Docket No. C-36,790C, and in Example 1, pp. 134-136 of International Publication No. WO90/03995, Attorney Docket No. C-36,790C-F which are both incorporated by reference.

The reaction of the PBO dope with the mixture of the title product and 4,6-diaminoresorcinol di(hydrogen chloride) is continued for 48 hours at 90° C., and then cooled to 50° C.. A 0.57-g(2.18 mmoles) portion of 1,4-diphenoxybenzene is added, followed by 88.60 grams of 10:1 methanesulfonic acid:phosphorus pentoxide solution added in two portions 30 minutes apart. The reaction is continued at 50° C. for 72 hours. A small portion of the reaction product dope can be placed upon a microscope slide and quenched with water and dried in air to yield a film of good strength and integrity having no visible phase separation.

A small quantity of the resulting block copolymer can be isolated as follows: it is coagulated in water, washed, dried, ground, rewashed and redried. This block copolymer has an inherent viscosity of 9.30 dL/g in methanesulfonic acid at 25° C. and 0.05 g/dL concentration.

EXAMPLE 4 Copolymerization of Difunctional Aryl Compound With p-Diphenoxybenzene In a N₂ atmosphere 0.76g of 4,6-diaminoresorcinol dihydrochloride and 3.00g of 1-(4-chlorocarbonylphenoxy)-4-(4-chlorosulfonylphenoxy) benzene are loaded into a 100 mL resin kettle which is sealed, transferred to a hood, and blanketed with N₂. This mixture is mechanically stirred and warmed with thermoregulated oil bath. A 55.0g portion of methanesulfonic acid/phosphorus pentoxide (10/1) mixture is added to the reactor. The reactor is kept at 70° C. for 2 hours under a N₂ atmosphere, then the temperature is increased to 90° C. and kept there for 16 hours under a N₂ atmosphere, then the reactor temperature is lowered to 50° C. with a 0.93-gram portion of p-diphenoxybenzene then added, along with 25.1 grams of the 10/1 methanesulfonic acid/phosphorus pentoxide solution, and kept at 50° C. for 48 hours under a N₂ atmosphere. At this point the reaction product becomes more viscous but it remains stirrable.

The product, a polyetherbenzoxazole sulfone, is represented by the following formula:

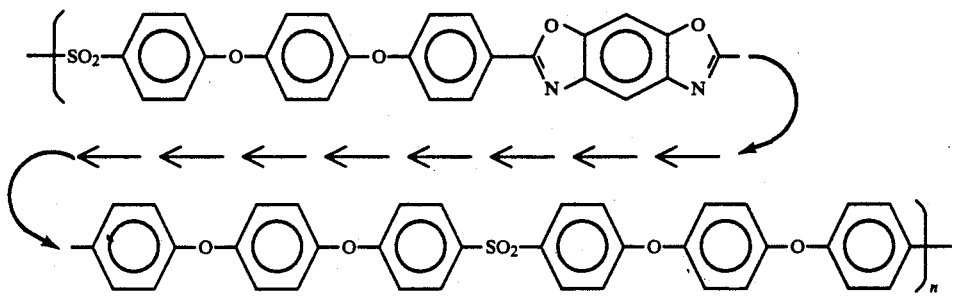

The reaction product is then precipitated with water in a blender as a beige fibrous solid that powders. The product is collected, then re-slurried with a touch of aqueous NaOH, then recollected. The product is washed 3 times with deionized water and dried to a constant weight in a 100° C. vacuum oven. The single point intrinsic viscosity of the product was found to be 0.40 dL/gram in methanesulfonic acid at 25.0° C.

EXAMPLE 5 Synthesis of Block Copolymer Containing Nonrigid Jointed PBO Sulfone Block and Poly (Aromatic Ether Sulfone) Thermoplastic Block Example 52 from pp. 180-183 of U.S. patent application Ser. No. 07/407,973 entitled "Copolymers Containing Polybenzoxazole, Polybenzothiazole and Polybenzimidazole Moieties" assigned to The Dow Chemical Company is incorporated by reference.

What is claimed is:

1. A difunctional aryl compound comprising:
   i) a carboxylic acid group or its acid halide, alkyl ester, amide, aryl ester, or thioester derivative,
   ii) a first aromatic group bonded to the carboxylic acid group or its acid halide, alkyl ester, amide, aryl ester, or thioester derivative,
   iii) a second aromatic group linked to the first aromatic group by a non-electron-withdrawing moiety which is an oxygen or sulfur atom,
   iv) a third aromatic group linked to the second aromatic group by a non-electron-withdrawing moiety which is an oxygen or sulfur atom, and
   v) a sulfonyl group or its acid halide, alkyl ester, amide, aryl ester, or thioester derivative bonded to the third aromatic group.

2. The difunctional aryl compound of claim 1 in which said non-electron-withdrawing moieties are affixed to their respective aromatic groups in a para position to each other with said aromatic groups being phenylene, said non-electron-withdrawing groups being oxygen atoms, said derivative of said sulfonyl group being sulfonic acid, and said derivative of said carboxylic acid group being the acid chloride of the formula:

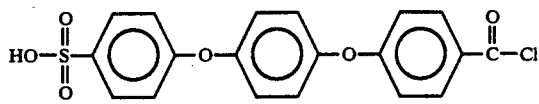

3. The difunctional aryl compound of claim 1 in which said aromatic groups are all phenylene rings.

4. The difunctional aryl compound of claim 1 in which there are more than three aromatic groups linked together by non-electron-withdrawing moieties.

5. The difunctional aryl compound of claim 1 in which said non-electron-withdrawing moieties are all oxygen.

6. The difunctional aryl compound of claim 1 in which said non-electron-withdrawing moieties are all sulfur.

7. The difunctional aryl compound of claim 1 in which said derivative of carboxylic acid is an acid halide.

8. The difunctional aryl compound of claim 7 in which said acid halide derivative of carboxylic acid is the acid chloride.

9. The difunctional aryl compound of claim 1 in which said derivative of carboxylic acid is a $C_1$-$C_6$ alkyl ester.

10. The difunctional aryl compound of claim 9 in which said $C_1$-$C_6$ alkyl ester derivative of carboxylic acid is the methyl ester.

11. The difunctional aryl compound of claim 9 in which said C1-C6 derivative of carboxylic acid is the ethyl ester.

12. The difunctional aryl compound of claim 1 in which said derivative of the sulfonyl group is a sulfonic acid group.

13. The difunctional aryl compound of claim 1 in which said derivative of the sulfonyl group is the acid halide of the sulfonic acid group.

14. The difunctional aryl compound of claim 1 in which said sulfonyl group or its derivative is the acid chloride derivative.

15. The difunctional aryl compound of claim 1 in which said derivative of the sulfonyl group is a $C_1$-$C_6$ alkyl ester.

16. The difunctional aryl compound of claim 15 in which said $C_1$-$C_6$ alkyl ester derivative of the sulfonyl group is the methyl ester.

17. The difunctional aryl compound of claim 15 in which said $C_1$-$C_6$ alkyl ester derivative of the sulfonyl group is the ethyl ester.

* * * * *